(12) United States Patent
Funke et al.

(10) Patent No.: US 10,465,334 B2
(45) Date of Patent: Nov. 5, 2019

(54) PROCESS FOR FINISHING TEXTILES

(71) Applicant: ARCHROMA IP GMBH, Reinach (CH)

(72) Inventors: Frank Funke, Ludwigshafen (DE); Tao Wang, Shanghai (CN); Sharon Tan, Singapore (SG)

(73) Assignee: ARCHROMA IP GMBH, Reinach (CH)

(*) Notice: Subject to any disclaimer, the term of this patent is extended or adjusted under 35 U.S.C. 154(b) by 209 days.

(21) Appl. No.: 15/127,405

(22) PCT Filed: Mar. 20, 2015

(86) PCT No.: PCT/EP2015/056003
§ 371 (c)(1),
(2) Date: Sep. 19, 2016

(87) PCT Pub. No.: WO2015/144600
PCT Pub. Date: Oct. 1, 2015

(65) Prior Publication Data
US 2018/0187369 A1   Jul. 5, 2018

(30) Foreign Application Priority Data
Mar. 24, 2014  (WO) ................ PCT/CN2014/073959

(51) Int. Cl.
*D06M 13/432* (2006.01)
*C07D 233/40* (2006.01)
*D06M 13/148* (2006.01)
*D06M 15/423* (2006.01)
*D06M 15/53* (2006.01)
*D06M 101/06* (2006.01)

(52) U.S. Cl.
CPC ......... *D06M 13/432* (2013.01); *C07D 233/40* (2013.01); *D06M 13/148* (2013.01); *D06M 15/423* (2013.01); *D06M 15/53* (2013.01); *D06M 2101/06* (2013.01); *D06M 2200/20* (2013.01)

(58) Field of Classification Search
CPC ..................... D06M 13/432; C07D 233/40
See application file for complete search history.

(56) References Cited

U.S. PATENT DOCUMENTS

| | | | |
|---|---|---|---|
| 3,112,156 A | 11/1963 | Vail et al. | |
| 4,295,846 A | 10/1981 | Petersen et al. | |
| 5,160,503 A * | 11/1992 | Smith | B27N 1/003 252/182.24 |
| 6,372,674 B1 | 4/2002 | Lack | |
| 2005/0234420 A1 | 10/2005 | Artley | |
| 2006/0090266 A1 | 5/2006 | Gardner et al. | |
| 2010/0099316 A1 | 4/2010 | Norenberg et al. | |
| 2014/0005295 A1 * | 1/2014 | Agrawal | A01N 59/16 523/122 |

FOREIGN PATENT DOCUMENTS

| | | |
|---|---|---|
| CN | 101663434 A | 3/2010 |
| EP | 0036076 A2 | 9/1981 |
| WO | 0039384 A1 | 7/2000 |

OTHER PUBLICATIONS

Frick, John G. et al., "Reaction of Dimethylurea and Glyoxal", Industrial & Engineering Chemistry Product Research and Development, Dec. 1, 1982, pp. 599-600, vol. 21, No. 4.

* cited by examiner

Primary Examiner — Peter F Godenschwager
(74) Attorney, Agent, or Firm — McBee Moore Woodward & Vanik IP, LLC

(57) ABSTRACT

Aqueous formulation comprising at least one alcohol A and at least one reaction product C of N,N'-substituted urea and glyoxal, wherein in the reaction product C at least 80 mol % of the hemiaminalic carbon atoms are bound to unetherified hydroxyl groups and wherein said alcohol A is different from reaction product C.

20 Claims, No Drawings

PROCESS FOR FINISHING TEXTILES

CROSS-REFERENCE TO RELATED APPLICATIONS

This application is a National Stage entry of International Application No. PCT/EP2015/056003, filed Mar. 20, 2015, which claims priority to Chinese Patent Application No. PCT/CN2014/073959, filed Mar. 24, 2014.

The present invention relates to aqueous formulations comprising at least one alcohol A and at least one reaction product C of N,N'-substituted urea and glyoxal.

There is a growing demand for textiles with wrinkle-free properties. At the same time textiles are increasingly required to contain little or no formaldehyde.

Wrinkle free properties of textiles have in the past been improved by finishing such textile with aminoplast resins like urea-formaldehyde resins or melamine formaldehyde resins.

WO 2000/39384 discloses processes for finishing textiles using different N-methylol ether group containing cross-linkers based for example on substituted urea. However, processes according to WO 2000/39384 yield textiles that comprise considerable amounts of formaldehyde.

US 2006/090,266 discloses a formaldehyde free process for finishing textiles using polyacids.

U.S. Pat. No. 4,295,846 discloses a process for the production of formaldehyde free finishing agents comprising reaction products of substituted urea with glyoxal that have been etherified in the 4- and 5-positions.

EP 36 076 discloses a process for making formaldehyde free finishing agents by reacting substituted urea and glyoxal and subsequent etherification of the reaction products.

All approaches previously applied for finishing textiles are insufficient with respect to the formaldehyde content, the wrinkle-free properties and/or the yellowing properties of the textiles obtained.

It was therefore an objective to provide a composition that is suitable for finishing textiles that contains little or no formaldehyde and that yields textiles with excellent wrinkle free properties.

The objective has been achieved by aqueous formulations comprising at least one alcohol and at least one reaction product C of N,N'-substituted urea and glyoxal, wherein in the reaction product C at least 80 mol % of the hemiaminalic carbon atoms are bound to unetherified hydroxyl groups.

Preferably the pH of aqueous formulations according to the invention is above, preferably from 4.5 to 6.8, more preferably 4.8 to 6.5 and even more preferably from 5 to 6.

Alcohol A is a compound different from reaction product C.

In a less preferred embodiment, alcohol A is a monoalcohol like methanol, ethanol or n/i-propanol.

Said alcohol A is normally a polyol comprising 2 or more hydroxy groups. Preferably alcohol A is a diol, triol, tetrol, pentaol of hexol.

In a particularly preferred embodiment alcohol A is a diol.

In a preferred embodiment, alcohol A is selected from glycerol, diethyleneglycol, propanediol, butanediol or alkoxylates thereof, especially ethoxylates thereof.

In one preferred embodiment alcohol A is 1,2-etanediol (glycerol).

In one preferred embodiment alcohol A is diethylene glycol (DEG).

In one preferred embodiment alcohol A is polyethyleneoxide.

In one preferred embodiment alcohol A is polyethyleneoxide comprising 3 to 10 units of ethylene oxide.

In one preferred embodiment alcohol A is polyethyleneoxide with an average molar mass Mw of 200 to 2000, preferably 300 to 1800, even more preferably 500 to 1500.

In another embodiment, alcohol A is triol.

In another embodiment, alcohol A is selected from trimethylol propane, glycerol or pentaerythritol.

In another embodiment, alcohol A is selected from ethoxylated trimethylol propane, glycerol or pentaerythritol bearing a molar average of 2 to 10 units of ethylene oxide per OH group.

In one embodiment, alcohols A are comprised in formulations according to the invention in an amount from 5 to 50% by weight, preferably 10 to 40 and more preferably 15 to 30% by weight. Such formulations are often used for storing and shipping and for preparing formulations that are to be applied on a textile substrate.

Suitable N,N'-substituted urea are especially those according to formula (I)

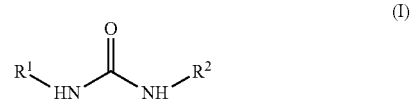

wherein $R^1$ and $R^2$ are independently selected from H, $C_1$ to $C_{18}$ alkyl or $[(CH_2)_n—O]_m—R^3$, with n=2 to 4, m=0 to 10 and $R^3$=H or $C_1$ to $C_4$ alkyl.

Preferably, the N,N'-substituted urea is selected from N,N'-dimethyl urea, N,N'-diethyl urea, N,N'-diisopropyl urea, N,N'-di n-butyl urea, N-methyl-N'-ethyl urea, N,N'-dihydroxyethyl urea, N,N'-dimethoxyethyl urea, N,N'-dimethoxypropyl urea.

Reaction product C is formed in a reaction between N,N'-substituted urea and glyoxal.

In one embodiment reaction products C correspond to the general formula (II)

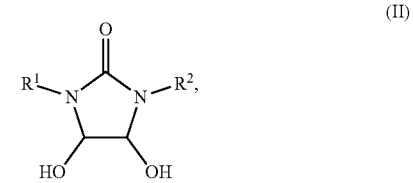

with $R^1$ and $R^2$ having the same meaning as defined above.

In one embodiment, formulations according to the invention comprise reaction product C in an amount from 5 to 65% by weight, preferably 10 to 60, more preferably 15 to 50 and even more preferably 20 to 40% by weight.

The combined content of reaction product C and alcohol A, even though they may not always be solid and without taking into account further additives, is herein referred to the solid content of a formulation.

In one embodiment, formulations according to the invention have a solid content of 10 to 70% by weight, preferably 20 to 65, more preferably 30 to 60 and even more preferably 50 to 60% by weight. Such formulations are often used for storing and shipping and for preparing formulations that are to be applied on a textile substrate.

In one embodiment, formulations according to the invention have a solid content of 5 to 35 by weight, preferably 10 to 30% by weight, even more preferably 15 to 25% by weight. Such formulations are often used for finishing textiles.

Normally, formulations according to the invention comprise 0.2 to 0.6, preferably 0.3 to 0.5 mol of alcohol A per mol of reaction product C.

It is in principle possible to use higher amounts of alcohol A, however, this will not improve the performance of the formulations and the finishing process.

Another aspect of the invention is a process for providing a formulation according to the invention comprising the following steps:
i) reacting at least one N,N'-substituted urea and glyoxal;
ii) adding an alcohol A to the mixture;
wherein the addition of alcohol A in step ii) is carried out such that essentially no etherification of the hemiaminalic OH groups of the product obtained in step i) takes place.

Preferably, processes for providing a formulation according to the invention comprise the following steps:
i) reacting at least one N,N'-substituted urea and glyoxal, wherein said reaction is carried out in aqueous medium at a pH from 4.5 to 6.8;
ii) adding an alcohol A to the mixture;
wherein the pH of the aqueous formulation is kept at a value of 4.5 or above after the addition of alcohol A in step ii).

More preferably, the pH of the aqueous formulation is kept at a value of 4.8 or above, even more preferably at a value of 5.0 or above after the addition of alcohol A in step ii)

In step i) reaction products C are formed. Reaction products C can be formed by reacting N,N'-substituted urea and glyoxal in aqueous medium at a pH from 4.5 to 6.8, preferably from 4.8 to 6.2.

In some cases buffer mixtures can be used to adjust the pH in aqueous media. Examples of suitable buffer mixtures include acetic acid/acetates, tartric acid/tartrates, citric acid/citrates, phthalic acid/phthalates, glycolic acid/glycolates, phosphoric acid/phosphates and mixtures thereof.

In a preferred embodiment, pH of the aqueous formulation is at no point below 4.0, preferably 4.5, more preferably below 4.8 and even more preferably 5.0.

After completion of the reaction, it is possible to set the pH to any desired value above 4.5, preferably above 4.8 and even more preferably above 5.0.

N,N'-substituted urea and glyoxal can for example be used in a molar ratio of 1.1:1 to 1:1. Preferably, the reaction is carried out such that after completion the reaction there is no residual free glyoxal. Preferably, an excess of glyoxal is avoided.

Glyoxal can for example be used as an aqueous solution.

The reaction between N,N'-substituted urea and glyoxal can for example be carried out at a temperature from 10° C. to 70° C., preferably 15 to 60° C. and even more preferably from 20 to 50° C.

In step ii), alcohol A is added to the mixture.

According to the invention, step ii) is carried out such that addition of the alcohol essentially leads to a mere physical mixture of alcohol A and reaction product C and that in particular essentially no etherification of the hemiaminalic OH groups takes place. "Hemiaminalic OH groups" in this context shall be understood to mean the OH-groups shown in formula (II) that are bound to the hemiaminalic carbon atom.

Preferably, more than 80 mol % of the hemiaminalic OH groups are unetherified, more preferably more than 90 mol %, even more preferably more than 95 mol % and especially preferably more than 95 mol %.

In one especially preferred embodiment, more than 99.9 mol % of the hemiaminalic OH groups are unetherified and present as OH groups.

The content of unetherified OH groups can be determined as described in the experimental part, by determining the amount of free, unetherified alcohol A by GC measurement and subtracting it from the amount of alcohol A originally added to the formulation.

To ensure that the hemiaminalic OH groups are not or only to a minor extent etherified, the pH of the aqueous formulation should be controlled and preferably maintained at a pH of 4.0 or above, preferably 4.5 or above, during and after the addition of alcohol A to the aqueous formulation until shortly before the application of the formulation on a textile.

Preferably the formulation is further maintained at a temperature below 100° C., preferably below 80° C., more preferably below 60° C. and especially preferably below 50° C. during and after the addition of alcohol A to the aqueous formulation. Preferably, the formulation is only exposed to temperatures above 100° C. after its application on a textile during the curing step.

Step ii) can in principle by carried out before, during or after carrying out step i), provided that the pH of the aqueous formulation is at no point after the addition of alcohol A below 4.5, preferably not below 4.8, even more preferably not below 5.0 and especially preferably not below 6.0.

Preferably, the addition of alcohol A is carried out after the formation of reaction product C is completed or essentially completed. "Essentially completed" in this context shall mean that more than 80 mol % of the carbonyl groups of glyoxal have reacted, preferably more than 90 mol % and even more preferably more than 95, 99 or 99.9 mol %.

The progress of the reaction can for example be monitored through the IR-absorption of the carbonylic CO group of glyoxal.

The addition of alcohol A to the mixture can for example be carried out at a temperature from 10 to 60° C., preferably 15 to 40° C., more preferably it is carried out a ambient temperature.

Another aspect of the invention is the use of formulations according to the invention for finishing textiles.

Preferably, such textiles comprise cotton, wool, cellulosic fibers, viscose, polyester, tencel, linen, modal, polylactide, polyamide or mixtures thereof.

Another aspect of the invention is a process for finishing textiles comprising the following steps Process for finishing textiles comprising the steps a) and c) to e):
a) providing at least one reaction product C of at least one N,N'-substituted urea and glyoxal in aqueous medium, wherein in the reaction product C at least 80 mol % of the hemiaminalic carbon atoms are bound to unetherified hydroxyl groups;
b) applying said reaction product C to the textile;
c) optionally removing some or all of the water;
d) curing.

In one preferred embodiment, processes according to the invention for finishing textiles comprise the following steps:
a) providing at least one reaction product C of at least one N,N'-substituted urea and glyoxal in aqueous medium, wherein in the reaction product C at least 80 mol % of the hemiaminalic carbon atoms are bound to unetherified hydroxyl groups,
b) providing at least one alcohol A,
c) applying the reaction product C and alcohol A to a textile substrate, d) optionally removing some or all of the water,
e) curing the mixture obtained in the previous steps and the textile substrate.

In one embodiment, alcohol A and reaction product C are applied to the textile using a formulation according to the invention.

In one embodiment, alcohol A and reaction product C are applied to the textile separately.

In one embodiment, alcohol A and reaction product C are applied to the textile simultaneously.

In one embodiment, alcohol A and reaction product C are applied to the textile subsequently.

In one preferred embodiment, processes according to the invention for finishing textiles comprise the following steps:
a) providing at least one reaction product C of at least one N,N'-substituted urea and glyoxal in aqueous medium, wherein in the reaction product C at least 80 mol % of the hemiaminalic carbon atoms are bound to unetherified hydroxyl groups,
b) adding at least one alcohol A to the mixture obtained in step a), wherein said aqueous mixture is preferably kept at a pH of 4.5 or above,
c) applying the formulation obtained in step b) to a textile substrate,
d) optionally removing some or all of the water,
e) curing the mixture obtained in the previous steps and the textile substrate.

Alcohol and reaction product C can be applied to the textile in a conventional manner generally known in the art like padding, spraying, or slop padding.

In case alcohol A is added into the mixture obtained in step a), this has to be done such that even after the addition of the alcohol A at least 80 mol % of the hemiaminalic carbon atoms in reaction product C are bound to unetherified hydroxyl groups.

While formulations according to the invention are normally stored at a pH above 4.5, it may be preferable to lower the pH of such formulations to a value of 3 to 5 or 4 to 5 shortly before the application on the textile. "Shortly" in this context means less than seven days, more preferably less than 1 day and even more preferably less than three hours and especially preferably less than 1 hour prior the application of a formulation to a textile.

In one embodiment, the pH of the aqueous formulation during the application step c) is 3 to 5, preferably 4 to 5 in the aqueous formulation. The pH of the textile, determined by placing a textile in demineralized water, applying ultrasound for 5 minutes and measuring the pH of the water, is normally 6 to 7 for the textile.

Normally, formulations applied on the textile in step c) have a solid content of 5 to 35% by weight, preferably 10 to 30% by weight, even more preferably 15 to 25% by weight.

Normally reaction product C and alcohol A are applied to the textile with an add on of 5 to 25 by weight, preferably 9 to 18% by weight on the fabric.

In a preferred embodiment, finishing catalysts are present during the steps c), d) and/or e). Suitable finishing catalysts are for example acid salts, ammonium salts of strong acids, magnesium chloride, zinc chloride, aluminium chloride, zinc nitrate, or salts of fluoroborates, mixtures of more than catalysts may also be used. In some cases it is advantageous to use mixtures of these catalysts with organic acids containing hydroxyl groups like glycolic acid. The amount of catalyst used is generally in the range of 25 to 45%, preferably 30 to 40% by weight relative to the solid content of the reaction product C used.

After padding of the reaction product C and the alcohol A in step c), the textile is squeezed to a wet pickup of 65 to 80%

The impregnated fabric (textile) can be dried more or less and can then be subjected to curing.

Preferably curing is achieved by subjecting the textile substrate comprising reaction product C and alcohol A to a temperature from 130 to 210° C., preferably 150 to 180° C.

Under these conditions, the curing process is normally completed after 20 seconds to 15 minutes. Normally a higher temperature requires shorter curing times and vice versa.

During or after drying and curing, the fabric can be shaped mechanically, for example by stuffing, crimping, ironing, calendaring, embossing, or pleating.

Processes for finishing textiles according to the invention comprise no formaldehyde in the add-on andare essentially formaldehyde free.

Processes for finishing textiles according to the invention allow for the production of textiles that comprise little or no formaldehyde, have excellent whiteness performance, anticrease properties, wrinkle resistance, shrink resistance, especially long-term anticrease, anti-wrinkle and antishrink properties, and high abrasion and rub fastnesses.

Especially cellulosic textiles finished according to the invention are long-term wrinkle and shrink resistance.

Processes for finishing textiles according to the invention are easy to carry out and very cost efficient and efficient with respect to the consumption of natural resources like water, energy or chemicals.

Processes for finishing textiles according to the invention are essentially a one step process with respect to the application onto the textile and do not require any further washing or treatment steps of the textile.

Compared to processes known from the art, processes for finishing textiles according to the invention require fewer washing and rinsing steps after the finishing process to remove formaldehyde intermediates of the finishing process.

Textiles that have been finished using formulations according to the invention and/or according to a finishing process according to the invention do not comprise any formaldehyde or only little formaldehyde, do not become yellow, have excellent whiteness performance, anticrease properties, wrinkle resistance, shrink resistance, especially long-term anticrease, anti-wrinkle and antishrink properties, and high abrasion and rub fastnesses. Especially cellulosic textiles finished according to the invention are long-term wrinkle and shrink resistance.

In particular, they maintain their anti-crease properties even over the long term and after many washing cycles.

Formulations according to the invention and finishing processes according to the invention can also be used in combination with further finishing agents customary in the art, like water repellents, softening, levelling and wetting agents, resin finishes, agents for modifying the hand.

Examples of water repellant agents are Fluorocarbons or paraffin wax emulsions or silicone containing formulations. Examples of softening agents are oxyethylation products of higher fatty acids, fatty alcohols, fatty acid amides, polyglycol ethers, higher fatty acids, fatty alcohol sulfonates, and N-stearyl-urea compounds.

Such further additives and adjuvants are normally used in amounts of 0.3 to 4.0% by weight, preferably 1 to 2.5% by weight, based on the weight of the dry textile. In some cases these amounts may be exceeded though.

EXAMPLES

All units and "parts" used herein are mass units or parts.

Amounts of free, unetherified polyol were determined by GC measurement of the aqueous mixtures.

For determining the content of free polyol, DEG in the present examples, 200 μg of the sample were placed in a flask and all solvent was removed in vacuum. The residual was redissolved in 20 ml of methanol and filtered through a 20 μm membrane for GC application. 1 μl of the mixture obtained were injected in a gas chromatography apparatus comprising a DB-WAXETR (30 m*0.25 mm*0.25 mm) column (inlet temperature 250° C., split ratio 10:1, wash vial methanol). The flow rate of the GC was 1 ml/min. Column temperature program: 150° C. to 230° C. (5 min) by 5° C./min, to 250° C. by 15° C./min.

Detector: FID 260° C.

To determine the absolute amount of DEG in the sample, the integral of the DEG signal was compared to that of a DEG standard solution.

Amounts of unetherified reaction products C were determined by subtracting the amount of free unetherified polyol from the amount of polyol originally added to the formulation.

Example 1: Formulation According to the Invention Comprising DEG 126 parts of N,N'-dimethyl urea are dissolved in 52 parts of water. 2 parts of phosphoric acid (85 mass % in water) and 3.2 parts of sodium hydroxide (25 mass %) in water) are added to adjust a pH of 6.3.

To this mixture, 183.7 parts of glyoxal (40% by weight in water) are added under cooling to keep the temperature below 35° C. After completion of the addition, the mixture is stirred at a temperature of 50° C. for four hours.

To this mixture, 80.9 parts of water and 49.5 parts of diethylene glycol (DEG) are added at ambient temperature and stirred for 30 minutes.

The amount of unetherified OH groups in the reaction product of N,N'-dimethyl urea and glyoxal was above 95 mol %.

Example 2: Formulation According to the Invention Comprising PEG 150

121.3 parts of N,N'-dimethyl urea are dissolved in 50 parts of water. 1.9 parts of phosphoric acid (85 mass % in water) and 3 parts of sodium hydroxide (25 mass % in water) are added to adjust a pH of 6.0.

To this mixture, 175.4 parts of glyoxal (40% by weight in water) are added under cooling to keep the temperature below 35° C. After completion of the addition, the mixture is stirred at a temperature of 50° C. for four hours.

To this mixture, 73.8 parts of water and 71.1 parts of polyethyleneoxide with an average molar mass Mw of 150 g/mol are added at ambient temperature and stirred for 30 minutes.

The amount of unetherified OH groups in the reaction product of N,N'-dimethyl urea and glyoxal was above 95 mol %.

Example 3: Formulation According to the Invention Comprising PEG 200

115.8 parts of N,N'-dimethyl urea are dissolved in 47.8 parts of water. 1.8 parts of phosphoric acid (85 mass % in water) and 2.9 parts of sodium hydroxide (25 mass % in water) are added to adjust a pH of 6.0.

To this mixture, 167.5 parts of glyoxal (40% by weight in water) are added under cooling to keep the temperature below 35° C. After completion of the addition, the mixture is stirred at a temperature of 50° C. for four hours.

To this mixture, 73.8 parts of water and 90.4 parts of polyethyleneoxide with an average molar mass Mw of 200 g/mol are added at ambient temperature and stirred for 30 minutes.

The amount of unetherified OH groups in the reaction product of N,N'-dimethyl urea and glyoxal was above 95 mol %.

Example 4 (Comparative Example)

121.3 parts of N,N'-dimethyl urea were dissolved in 50 parts of water. 1.9 parts of phosphoric acid (85 mass % in water) and 3 parts of sodium hydroxide (25 mass % in water) were added to adjust a pH of 6.0.

To this mixture, 175.4 parts of glyoxal (40% by weight in water) were added under cooling to keep the temperature below 35° C. After completion of the addition, the mixture was stirred at a temperature of 50° C. for four hours. The mixture was then diluted with 73.8 parts of water.

No alcohol was added.

Example 5 (Comparative Example)

820 parts of a 40% by weight solution of N,N'-dimethyl 4,5-dihydroxyethyleneurea in water and 180 parts of polyethylene oxide with an average molecular mass Mw of 200 g/mol are placed in a pressure vessel. The solution obtained was heated to 120° C. for 30 minutes.

The amount of etherified OH groups in the reaction product of N,N'-dimethyl urea and glyoxal was 30 mol %.

Application Examples A1 to A15

A textile material (column c) was padded in a conventional manner with a liquor comprising:

1 g/l of Polyethyleneoxide mono-2-propyl-1-heptyl ether, CAS Number: 160875-66-1

20 g/l magnesium chloride hexahydrate 20 g/l of a 30% by weight polyethylene wax emulsion 30 g/l of a 10% by weight emulsion of polysiloxane comprising aminoalkyl groups emulsion Formulations obtained according to examples 1 to 5 (column a) were used telquel and were comprised in said liquor in amounts given in table 1(column b)

The so obtained textile material was squeezed to a wet pick-up of 70%, dried at 90 to 110° C. to 6-8% residual moisture and heated to 170° C. for 45 seconds.

The textile, formulations and concentrations used as well as the properties of the textile obtained are given in table 1.

a: Crosslinker used, the number indicates the respective example b: Amount of the formulation obtained in the respective examples 1 to 5 used in the liquor c: textile material used The finished fabric had the following properties:

f: DP rating (AATCC™ 124)

g: Tear strength (ISO 13937-1)

h: Tensile strength (ISO 13934-1)

i: whiteness (Berger) on bleached fabric, measured on Spectraflash 500 j: Abrasion ASTM D 4966-98, (9 Kpa)

k: Formaldehyde content of the textile obtained in ppm (AATCC 112)

TABLE 1

Application experiments A1 to A15 and properties of the finished textiles obtained.

| No. | a | b | c | f | g | h | i | j | k |
|---|---|---|---|---|---|---|---|---|---|
| A1 | 1 | 400 g/l | bleached 100% cotton poplin | 3.5 | −31% | −52% | −5.5 | −33% | <16 |
| A2 | 2 | 400 g/L | bleached 100% cotton poplin | 3.5 | −36% | −57% | −5.1 | −40% | <16 |
| A3 | 3 | 400 g/L | bleached 100% cotton poplin | 3.5 | −34% | −54% | −4.7 | −45% | <16 |
| A5 | 3 | 400 g/L | viscose | 3.5 | −32% | 272% | | | <16 |
| A6 | 3 | 440 g/L | viscose | 3.5 | −31% | 249% | | | <16 |
| A7 | 3 | 350 g/L | cotton twill, 80s/2 * 80s/2, 130 * 90 blue | 3.5 | −25% | −31% | | −11% | <16 |
| A8 | 3 | 350 g/L | cotton twill, 80s/2 * 80s/2, 130 * 90 red | 3.5 | −57% | −35% | | −31% | <16 |
| A9 | 3 | 200 g/L | 65% Cotton 35% Polyester blend | 3.5 | −1% | −8% | | | <16 |
| A10 | 3 | 300 g/L | 65% Cotton 35% Polyester blend | 3.5 | −11% | −11% | | | <16 |
| A11 | 3 | 300 g/L | 100% cotton 60/1 | 3.5 | −39% | −35% | | | <16 |
| A12 | 3 | 300 g/L | 100% cotton 50/1 | 3.5 | −28% | −32% | | | <16 |
| A14 | 4 | 400 g/L | bleached 100% cotton poplin | 3 | −55% | −39% | −5.3 | −50% | <16 |
| A15 | 5 | 400 g/L | bleached 100% cotton poplin | 3 | | | −5.4 | | <16 |

The invention claimed is:

1. An aqueous formulation comprising at least one alcohol A and at least one reaction product C of N,N'-substituted urea and glyoxal, wherein in the reaction product C at least 80 mol % of the hemiaminalic carbon atoms are bound to unetherified hydroxyl groups and wherein said alcohol A is different from reaction product C,
wherein said N,N'-substituted urea is a compound according to formula (I)

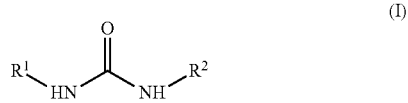

wherein $R^1$ and $R^2$ are independently selected from H, $C_1$ to $C_{18}$ alkyl or $[(CH_2)_n—O]_m—R^3$, with n=2 to 4, m=0 to 10 and $R^3$=H or $C_1$ to $C_4$ alkyl, and
wherein said alcohol A is ethylene glycol or polyethylene glycol.

2. The formulation according to claim 1, wherein pH of said formulation is above 4.5.

3. The formulation according to claim 1, wherein said alcohol A is ethylene glycol.

4. The formulation according to claim 1, wherein said alcohol A is polyethylene glycol.

5. The formulation according to claim 1, wherein said N,N'-substituted urea is selected from the group consisting of N,N'-dimethyl urea, N,N'-diethyl urea, N,N'-diisopropyl urea, N,N'-di n-butyl urea, N-methyl-N'-ethyl urea, N,N'-dihydroxyethyl urea, N,N'-dimethoxyethyl urea, and N,N'-dimethoxypropyl urea.

6. The formulation according to claim 1, wherein solid content of the formulation is 10 to 70% by weight based on the formulation.

7. The formulation according to claim 1 obtained according to a process comprising
   (i) reacting at least one N,N'-substituted urea of formula (I) and glyoxal;
   (ii) adding an alcohol A to the mixture;
   wherein said alcohol A is ethylene glycol or polyethylene glycol and wherein addition of alcohol A in ii) is carried out such that more than 80 mol % of the hemiaminalic OH groups are unetherified,
   wherein said formulation is for finishing a textile.

8. The formulation according to claim 7, wherein addition of alcohol A in ii) is carried out such that more than 90 mol % of the hemiaminalic OH groups are unetherified.

9. The formulation according to claim 7, wherein addition of alcohol A in ii) is carried out such that more than 95 mol % of the hemiaminalic OH groups are unetherified.

10. The formulation according to claim 7, wherein addition of alcohol A in ii) is carried out such that more than 99.9 mol % of the hemiaminalic OH groups are unetherified.

11. The formulation according to claim 1, wherein pH of said formulation is in a range from 5 to 6.

12. The formulation according to claim 1, wherein a ratio of mol of alcohol A to mol of reaction product C is in a range from 0.2:1 to 0.6:1.

13. The formulation according to claim 1, wherein a ratio of mol of alcohol A to mol of reaction product C is in a range from 0.3:1 to 0.5:1.

14. A process for providing the formulation according to claim 1 comprising:
   i) reacting at least one N,N'-substituted urea of formula (I) and glyoxal;
   ii) adding an alcohol A to the mixture;
   wherein the addition of alcohol A in ii) is carried out such that essentially no etherification of the hemiaminalic OH groups of the product obtained in i) takes place.

15. A process for providing the formulation according to claim 1 comprising:

i) reacting at least one N,N'-substituted urea of formula (I) and glyoxal, wherein said reaction is carried out in aqueous medium at a pH from 4.5 to 6.8;

ii) adding an alcohol A to the mixture;

wherein pH of the aqueous formulation is kept at a value of 4.5 or above after addition of alcohol A in ii).

16. A process for finishing a textile comprising:
a) providing the aqueous formulation of claim 1;
c) applying said aqueous formulation to the textile;
d) optionally removing some or all water;
e) curing.

17. The process according to claim 16 comprising:
a) providing the aqueous formulation of claim 1,
c) applying the aqueous formulation to a textile substrate,
d) removing some or all water,
e) curing the mixture obtained and the textile substrate.

18. The process according to claim 16, wherein said curing is achieved by subjecting the textile to a temperature from 100 to 170° C.

19. The process according to claim 16, wherein said aqueous formulation is set to a pH of 3 to 5 shortly before application on the textile.

20. A textile that has been finished according to claim 16.

* * * * *